United States Patent [19]
Eason et al.

[11] Patent Number: 5,447,607
[45] Date of Patent: Sep. 5, 1995

[54] ETHER RECOVERY

[75] Inventors: John H. Eason, Katy, Tex.; Joseph Klepac, Krotz Springs, La.

[73] Assignee: Phillips Petroleum Company, Bartlesville, Okla.

[21] Appl. No.: 247,203

[22] Filed: May 20, 1994

Related U.S. Application Data

[62] Division of Ser. No. 998,706, Dec. 30, 1992, Pat. No. 5,329,051.

[51] Int. Cl.⁶ .................. B01D 3/14; C07C 41/34; C07C 41/38
[52] U.S. Cl. .................. 202/154; 202/155; 203/14; 203/45; 203/46; 203/71; 203/DIG. 16; 568/699
[58] Field of Search .............. 203/14, 71, DIG. 16, 203/DIG. 13, 43, 44, 45, 46, 73, DIG. 23; 568/699; 202/152, 154, 155, 172

[56] References Cited

U.S. PATENT DOCUMENTS

| | | | |
|---|---|---|---|
| 4,014,667 | 3/1977 | Barber | 203/18 |
| 4,346,241 | 8/1982 | Feldman | 203/22 |
| 4,399,000 | 8/1983 | Tedder | 203/18 |
| 4,544,776 | 10/1985 | Osterburg et al. | 203/DIG. 19 |
| 4,770,780 | 9/1988 | Moses | 203/16 |
| 5,167,937 | 12/1992 | Harandi et al. | 203/DIG. 6 |

Primary Examiner—Virginia Manoharan
Attorney, Agent, or Firm—George E. Bogatie

[57] ABSTRACT

Process equipment is provided for separating ether, alcohol and hydrocarbon components from various etherifications of $C_4$ or $C_5$ isoolefins with an alcohol such as methanol or ethanol, and wherein identical process vessels are utilized for recovery of MTBE, ETBE, TAME, or TAEE. In use the process vessels are serially arranged in three zones. The first zone includes a first water wash vessel followed by a first fractionator and provides the ether product, the second zone includes a second wash vessel followed by a hydrocarbon stripper and recovers a stabilized hydrocarbon stream, the third zone includes a second fractionator which recovers an alcohol suitable for recycling.

6 Claims, 1 Drawing Sheet

ETHER RECOVERY

This is a division of application Ser. No. 07/998,706, filed Dec. 30, 1992 now U.S. Pat. No. 5,329,051.

This invention relates to the recovery of ethers from a reaction mixture. In one aspect it relates to liquid-liquid contact means for separating reactor effluent in the preparation of tertiary alkyl ethers. In another aspect this invention relates to an arrangement of columns designed for extracting alcohol with water.

BACKGROUND OF THE INVENTION

It is known that tertiary alkyl ethers, which are high octane blending components for motor fuels, can be prepared by reacting a primary alcohol with an olefin having a double bond on a tertiary carbon atom. For example, methanol reacts with isobutylene or isoamylene to form respectively methyl tert-butyl ether (MTBE) and tert-amyl methyl ether (TAME). Similar reactions are known which produce ethyl tert-butyl ether (ETBE) and tert-amyl ethyl ether (TAEE). Reference is had to U.S. Pat. Nos. 4,071,567; 3,979,461; 3,135,807; 3,846,088; among many others.

These ether reactions are so selective for tertiary olefins that they constitute a valid process for the removal from olefinic streams where they are encountered together with linear olefins. When producing such ethers however, it is desirable to remove the unreacted alcohol from the ether in the direction effluent and recycle it to the ether reactor.

A variety of processes are known for the separation of alcohol from tertiary alkyl ether products. All of the known individual processes, however, fail to provide the flexibility of separating alcohol from a number of difference ether products such as MTBE, ETBE, TAME and TAEE.

Accordingly it is an object of this invention to provide an apparatus which will recover alcohol from a reaction mixture containing a tertiary alkyl ether.

Another object of this invention is to provide an improved arrangement of columns for extracting alcohol with water.

Another object of this invention is to employ essentially identical process equipment to separate MTBE, TAME, ETBE or TAEE reaction products.

Still another object of this invention is to recover unreacted hydrocarbons from a tert-alkyl ether reaction product.

BRIEF SUMMARY OF THE INVENTION

In accordance with this invention there is provided apparatus for separating alcohol from a reaction effluent stream in the etherification of $C_4$ or $C_5$ isoolefins, which apparatus employs essentially the same process equipment to separate a variety of ether compounds such as MTBE, ETBE, TAME or TAEE or mixtures thereof. The process which uses the apparatus features dual water wash steps plus fractionation, the entire reaction product from a tertiary alkyl ether reaction containing the high octane ether components, along with hydrocarbons which include unreacted $C_4$ or $C_5$ isoolefins and inert hydrocarbons such as linear olefins and paraffins and also unreacted alcohol, is separated in a first separation zone to provide a product stream containing the ether component, a stream containing a water/alcohol mixture and a stream primarily containing hydrocarbons but also containing alcohol. This later stream of hydrocarbons containing alcohol is further separated in a second separation zone to provide a hydrocarbon product stream for further utilization as desired, and a water/alcohol mixture stream which is combined with the water/alcohol mixture stream of the first separation zone. The combined water/alcohol mixture stream is separated in a third separation zone to provide an alcohol product stream which is suitable for recycle to the ether reactor and a water stream which is suitable for other uses.

In a preferred embodiment the first separation zone includes a water extraction step followed by fractionation of ether in which the water extraction step removes a first portion of alcohol from the reaction effluent. Accordingly, this water extraction yields an extract containing alcohol and a raffinate containing the ether, hydrocarbons and also containing lesser amounts of alcohol carried over with the hydrocarbons. This raffinate is passed to the other fractionator to yield the ether product in a bottom stream and an overhead stream containing hydrocarbons and alcohol which is passed to the second separation zone.

The second separation zones includes a water extraction step followed by a hydrocarbon stripping operation. This extraction step in the second separation zone removes a second portion of alcohol which is essentially all of the remaining alcohol in the reaction effluent, and is employed to further reduce alcohol losses. Accordingly, the water extraction in the second separation zone yields an extract containing alcohol and a raffinate containing hydrocarbons with essentially no alcohol. This raffinate stream is passed to a hydrocarbon stripper column for further purification and produces a stabilized hydrocarbon stream.

The third separation zone is an alcohol fractionation yielding products of ether and water separated from water/alcohol mixtures obtained from the first and second separation zones.

Other objects, aspects as well as the several advantages of the invention will be apparent particularly in the art upon reading the specification and the appended claims and the drawing in which:

DETAILED DESCRIPTION OF THE INVENTION

Figure 1:
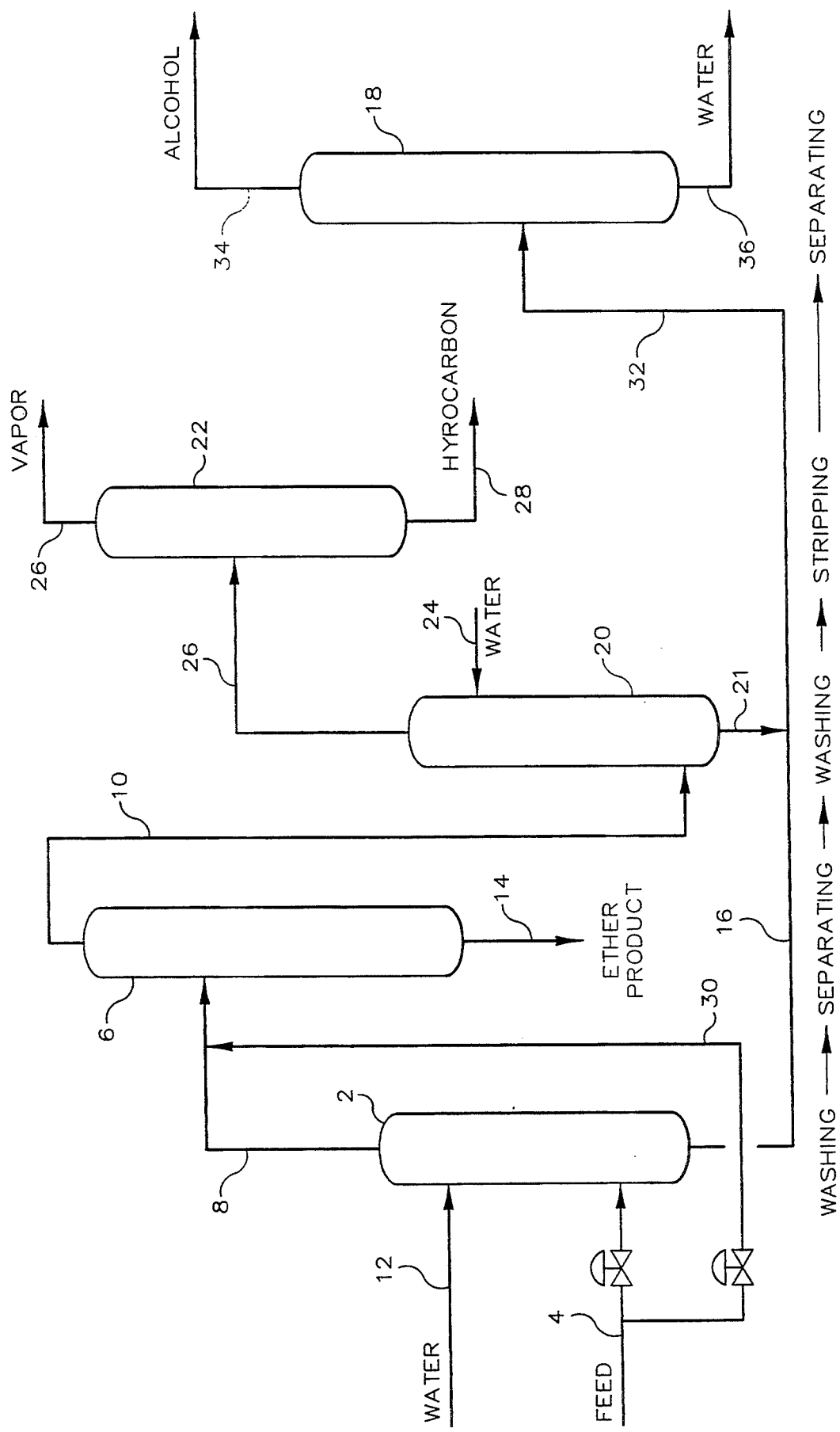
FIG. 1 is a simplified schematic illustration showing a process flow and arrangement of apparatus according to a preferred embodiment of this invention.

It will be appreciated by those skilled in the art that since FIG. 1 is schematic only many items of equipment which would be needed in a commercial plant for successful operation have been omitted for the sake of clarity. Such items of equipment would include for example, flow, pressure, and temperature measuring instruments with corresponding process controllers; pumps, heat exchangers, valves, etc. all these items would be provided in accordance with standard chemical engineering practice, whoever, they play no part in the explanation of the present invention.

Referring now to FIG. 1 the entire reaction produce of a reaction that selectively reacts a tertiary olefin having 4 or 5 carbon atoms per molecule with an alcohol (e.g. methanol or ethanol) to produce an ether, is feed via conduit 4 to a first separation zone which includes an extraction column 2 and a fractionator 6. This reaction effluent supplied via conduit 4 contains a product tertiary alkyl ether in an excess of unreacted and inert hydrocarbons and also contains unreacted alcohol. The extraction column or so called water washing operation, involves counter currently contacting the feed material with water supplied via conduit 12 at a temperature typically about 40° C. and a gauge pressure e.g. 1000 to 1200 kPa, which is sufficient to keep the hydrocarbons in the liquid phase.

A first portion of the unreacted alcohol comprising at least about 50 wt. % of the alcohol in the feed is removed in the extraction step in the first separation zone. While not wishing to be limited by theory, it is thought that sufficient alcohol is removed from the feed material by the water extraction step carried out in extraction column 2 such that operation of the ether fractionator 6, which follows, is enhanced either because the separation factors of the remaining components are improved or because the ether fractionator 6 does not operate in an ether/alcohol/hydrocarbon azeotrope. The overhead raffinate from the extraction in column 2 contains principally inert hydrocarbons plus the product ether together with the lesser amounts of unreacted isoolefins and alcohol. This raffinate stream is passed to a distillation column 6 via conduit 8 from which is recovered an overhead stream in conduit 10 containing hydrocarbon plus lesser quantities of alcohol. The bottom stream in conduit 14 recovers the product ether for use such as a high octane blending component for motor fuel.

The extract bottoms from the water wash operation in extraction column 2 contains a mixture of water and alcohol where the total amount of alcohol comprises a concentration of about 20% by weight of the total stream. This stream is passed via conduits 16 and 32 to an alcohol fractionator 18.

A bypass conduit 30 around the extraction column(2), is provided for excluding the water wash column 2 when processing MTBE.

The overhead hydrocarbon phase withdrawn from the ether fractionator 6 is passed to the second separation zone where additional alcohol may be recovered while purity of the hydrocarbon stream is improved. The second separation zone includes water extraction column 20 and stripper column 22. The overhead stream withdrawn from fractionator 6 is passed via conduit 10 to extraction column 20 into which water is introduced via conduit 24. A hydrocarbon raffinate stream being substantially free of alcohol is withdrawn from column 20 via conduit 26, and an alcohol/water mixture is withdrawn via conduit 21 and combined with a stream of similar composition in conduit 16. Further purification of the overhead hydrocarbon stream so as to meet certain purity specification is provided in stripper column 22, where the lighter fractions are removed from the hydrocarbons via conduit 26 and a stabilized hydrocarbon product is removed via conduit 28.

The water/alcohol mixture supplied to fractionator 18 via conduit 32 is separated in fractionator 18 to provide an alcohol stream in conduit 34 which is suitable for recycle to the ether reactor, and a water stream in conduit 36 which is suitable for recycle to extractors 2 and/or 20. While actual operating conditions for the individual units illustrated in FIG. 1 will depend to some extent on the make-up of the feed, typical operating conditions of the individual units of the ether recovery operation are given in Table I below, where the numbers in parenthesis correspond to the reference numerals in FIG. 1.

TABLE I

| Typical Operating Conditions | |
| --- | --- |
| Extractor (2) | |
| Temp °C. | 40 |
| Gauge Press. kPa | 1100 |
| Fractionator (6) | |
| Temperature °C. | |
| Top | 50–60 |
| Bottom | 110–160 |
| Gauge Pressures kPa | |
| Top | 540–740 |
| Bottom | 580–770 |
| Extractor (20) | |
| Temp °C. | 38 |
| Press. kPa | 827 |
| Stripper (22) | |
| Temp °C. | 50–70 |
| Gauge Press. kPa | 540–1360 |
| Fractionator (18) | |
| Temperature °C. | |
| Top | 76–103 |
| Bottom | 116–130 |
| Gauge Pressures kPa | |
| Top | 158 |
| Bottom | 172 |

The present invention is applicable to a variety of ether forming units where the above described dual washing steps in combination with fractionations provide the novel elements. In operation the first extractor 2 can remove at least about 50 wt. % and preferably about 75 wt. % of the alcohol contained in the feed, which as previously stated can be sufficient alcohol removal to prevent an ether/alcohol/hydrocarbon azeotrope from forming in fractionator 6 for reaction products comprising ETBE, TAME, and TAEE or mixtures thereof, thus improving separation in fractionator 6. Additional alcohol is then removed in a second water extraction 20.

Reasonable variations and modifications, which will become apparent to those skilled in the art, can be made in this invention. Such modifications and variations are within the scope of the described invention and the appended claims.

That which is claimed is:

1. Apparatus for separating material constituents in an etherification reaction effluent stream consisting essentially of tertiary alkyl ether, hydrocarbons including unreacted isoolefins and inert hydrocarbons, and unreacted alcohol, said apparatus comprising:
   (a) a first water extraction means;
   (b) means for introducing water into said first water extraction means;
   (c) means for introducing said reaction effluent stream into said first water extraction means for providing a first stream comprising an extract mixture of alcohol and water, and a second stream comprising a raffinate mixture of said ether, said hydrocarbons, and said unreacted alcohol;
   (d) a first fractionation means;
   (e) means for introducing said second stream as a feed stream to said first fractionation means, wherein said second stream is fractionated to provide a third stream consisting essentially of said ether substantially free of alcohol, and a fourth stream consisting essentially of a mixture of said hydrocarbons, said unreacted alcohol and water;
   (f) a second water extraction means;

(g) means for introducing water into said second water extraction means;

(h) means for introducing said fourth stream into said second water extraction means for providing a fifth stream consisting essentially of an extract mixture of alcohol and water, and a sixth stream consisting essentially of a raffinate of said hydrocarbons substantially free of alcohol;

(i) a second fractionation means; and (j) means for combining said first stream and said fifth stream to form a seventh stream, and means for introducing said seventh stream as a feed stream to said second fractionation means where said seventh stream is fractionated to provide an overhead stream consisting essentially of said unreacted alcohol and a bottom stream consisting essentially of water.

2. Apparatus in accordance with claim 1 wherein said alcohol is selected from the group consisting essentially of methanol and ethanol.

3. Apparatus in accordance with the claim 1 wherein said unreacted hydrocarbons comprise $C_4$ or $C_5$ isoolefins and said inert hydrocarbons comprise paraffins and linear olefins.

4. Apparatus in accordance with claim 1, said apparatus additionally comprising:

a stripping column;

means for introducing said sixth stream as a feed stream for said stripping column wherein said sixth stream is stripped of light ends to produce a hydrocarbon stream.

5. An apparatus in accordance with claim 1, wherein said tertiary alkyl ether is selected from the group consisting of methyl tert-butyl ether (MTBE), tert-amyl methyl ether (TAME), ethyl tert-butyl ether (ETBE) and tert-amyl ethyl ether (TAEE).

6. Apparatus in accordance with claim 1 additionally comprising:

a bypass means around said first water extraction means to facilitate bypassing of said reaction effluent stream around said first extraction means.

* * * * *